(12) United States Patent
Kim et al.

(10) Patent No.: US 11,149,281 B2
(45) Date of Patent: Oct. 19, 2021

(54) METHOD FOR PRODUCING GENOME-MODIFIED PLANTS FROM PLANT PROTOPLASTS AT HIGH EFFICIENCY

(71) Applicants: INSTITUTE FOR BASIC SCIENCE, Daejeon (KR); SEOUL NATIONAL UNIVERSITY R&DB FOUNDATION, Seoul (KR); AICT, Suwon-si (KR)

(72) Inventors: Jin Soo Kim, Seoul (KR); Jungeun Kim, Seoul (KR); Sunghwa Choe, Gimpo-si (KR); Je Wook Woo, Daejeon (KR); Soon Il Kwon, Gunpo-si (KR); Hyeran Kim, Daejeon (KR)

(73) Assignees: INSTITUTE FOR BASIC SCIENCE, Daejeon (KR); SEOUL NATIONAL UNIVERSITY R&DB FOUNDATION, Seoul (KR); AICT, Suwon-si (KR)

(*) Notice: Subject to any disclaimer, the term of this patent is extended or adjusted under 35 U.S.C. 154(b) by 5 days.

(21) Appl. No.: 15/766,445

(22) PCT Filed: Oct. 6, 2016

(86) PCT No.: PCT/KR2016/011216
§ 371 (c)(1),
(2) Date: Apr. 6, 2018

(87) PCT Pub. No.: WO2017/061805
PCT Pub. Date: Apr. 13, 2017

(65) Prior Publication Data
US 2019/0338298 A1 Nov. 7, 2019

(30) Foreign Application Priority Data

Oct. 6, 2015 (KR) .................. 10-2015-0140314
Oct. 6, 2016 (KR) .................. 10-2016-0129356

(51) Int. Cl.
*C12N 15/82* (2006.01)
*C12N 9/22* (2006.01)
*C12N 15/11* (2006.01)

(52) U.S. Cl.
CPC ........... *C12N 15/8213* (2013.01); *C12N 9/22* (2013.01); *C12N 15/11* (2013.01); *C12N 15/8206* (2013.01); *C12N 15/8207* (2013.01); *C12N 15/8298* (2013.01); *C12N 2310/20* (2017.05); *C12N 2800/80* (2013.01)

(58) Field of Classification Search
CPC ... C12N 15/8298; C12N 15/8213; A01H 5/12
See application file for complete search history.

(56) References Cited

U.S. PATENT DOCUMENTS

| 5,917,128 A * | 6/1999 | Barten ..................... C12N 5/14 800/303 |
| 6,997,297 B2 | 2/2006 | Bartley et al. |
| 7,250,559 B2 * | 7/2007 | Quiros ..................... C12N 9/00 435/320.1 |
| 8,367,256 B2 | 2/2013 | Jahnke et al. |
| 2009/0013433 A1 | 1/2009 | Wang et al. |
| 2014/0295556 A1 | 10/2014 | Joung et al. |
| 2015/0071903 A1 | 3/2015 | Liu et al. |
| 2015/0284727 A1 | 10/2015 | Kim et al. |

FOREIGN PATENT DOCUMENTS

| CN | 102618554 | 8/2012 |
| CN | 103343120 | 10/2013 |
| JP | 04-502860 | 5/1992 |
| JP | 2015-527081 | 9/2015 |
| KR | WO 2014/065596 | * 5/2014 ............ C12N 15/11 |
| KR | 10-2015-0101446 | 9/2015 |
| KR | 10-2016-0011217 | 1/2016 |
| WO | 2014/039684 | 3/2014 |
| WO | 2014/065596 | 5/2014 |
| WO | 2014/191518 | 12/2014 |
| WO | 2014/194190 | 12/2014 |
| WO | 2014/199358 | 12/2014 |
| WO | 2017/061806 | 4/2017 |

OTHER PUBLICATIONS

Lelivelt C. et al. Plant Molecular Biology, (2005) vol. 58: pp. 763-774. (Year: 2005).*
K. Xie et al., "RNA-Guided Genome Editing in Plants Using a CRISPR-Cas System", Molecular Plant, vol. 6, No. 6, pp. 1975-1983, Nov. 2013.
K. Belhaj et al., "Plant genome editing made easy: targeted mutagenesis in model and crop plants using the CRISPR/Cas system", Plant Methods, vol. 9, No. 39, pp. 1-10, 2013.
Feng et al., "Efficient genome editing in plants using a CRISPR/Cas", Cell Research, vol. 23, pp. 1229-1232, 2013.
C. N. Kanchiswamy et al., "Non-GMO genetically edited crop plants", Trends in Biotechnology, vol. 33, pp. 489-491, 2015.
S. Luo et al., "Non-transgenic plant genome editing using purified sequence-specific nucleases", Molecular Plant, vol. 8, pp. 1425-1427, 2015.
S.W. Cho et al., "Heritable gene knockout in Caenorhabditis elegans by Direct Injection of Cas9-sgRNA Ribonucleoprotins", Genetics, vol. 195, pp. 1177-1180, Nov. 2013.

(Continued)

*Primary Examiner* — Russell Kallis
(74) *Attorney, Agent, or Firm* — Lex IP Meister, PLLC

(57) ABSTRACT

The present invention relates to a method of increasing the production efficiency of gene-edited plants, regenerated from plant protoplasts, by use of a Cas protein-guide RNA ribonucleoprotein (RNP). According to the present invention, the method of increasing the production efficiency of gene-edited plants makes it possible to efficiently produce target gene-mutated plants and to minimize the introduction of foreign DNA into plants. Thus, the present invention can be very advantageously used in a wide variety of fields, including agriculture, food and biotechnology.

15 Claims, 7 Drawing Sheets

Specification includes a Sequence Listing.

(56) References Cited

OTHER PUBLICATIONS

J.-S. Lee et al., "RNA-guided genome editing in *Drosophila* with the purified Cas9 protein", G3: Genes, Genomes, Genetics, vol. 4, 1291-1295, Jul. 2014.
Y.H. Sung et al., "Highly efficient gene knockout in mice and zebrafish with RNA-guided endonucleases", Genome Research, vol. 24, pp. 125-131, 2014.
S. Kim et al., "Highly efficient RNA-guided genome editing in human cells via delivery of purified Cas9 ribonucleoproteins", Genome Research, vol. 24, pp. 1012-1019, 2014.
Y. Morinaka et al., "Morphological alteration Caused by Brassinosteroid Insensitivity Increases the Biomass and Grain Production of Rice", Plant Physiology, vol. 141, pp. 924-931, Jul. 2006.
Japan Patent Office, Office Action of JP 2018-532043 dated Sep. 4, 2018.
Canadian Intellectual Property Office, Office Action of CA 3,001,232 dated Aug. 10, 2018.
IP Australia, Office Action of AU 2016336565 dated Jun. 27, 2018.
Jones, H.D., "Regulatory uncertainty over genome editing", Nature Plants, 2015, vol. 1, Article No. 14011.
Kim, S. et al., "Highly efficient RNA-guided genome editing in human cells via delivery of purified Cas9 ribonucleoproteins", Genome research, 2014, vol. 24 pp. 1012-1019.
Hyun, Y. et al., "Site-directed Mutagenesis in *Arabidopsis thaliana* Using Dividing Tissue-targeted RGEN of the CRISPR/Cas System to Generate Heritable Null Alleles", Planta, 2015, vol. 241, pp. 271-284.
Yang, C. et al., "The Mechanisms of Brassinosteroids Action: from Signal Transduction to Plant Development", Molecular Plant, vol. 4, No. 4, Jul. 1, 2011, pp. 588-600.
Edited by Yu Lijie et al. Course for Plant Tissue Culture (1st edition), Huazhong University of Science and Technology Press, pp. 133-134, Jul. 31, 2015.
SIPO, Office Action of CN Patent Application No. 201680065239.4, dated Mar. 5, 2019.
Serry Koh et al., "T-DNA tagged knockout mutation of rice OsGSK1, an orthologue of *Arabidopsis* BIN2, with enhanced tolerance to various abiotic stresses", Plant Molecular Biology, vol. 65, No. 4, pp. 453-466, Aug. 2007.
EPO, Extended European Search Report of EP 16853921 dated Feb. 18, 2019.
T. Mizutani et al., "Plant Regeneration and Cell Fusion of Protoplasts from Lettuce Cultivars and Related Wild Species in Japan", Saga University agricultural department bulletin, 1989, No. 67, p. 109-118.
Y. Fujimoto et al., "Production of somatic hybrid plants between cultivars in *Lactuca sativa* through electrofusion" Japanese Journal of Breeding , 1988, vol. 38, p. 52-53.
JPO, Office Action of JP Patent Application No. 2018-532043 dated Dec. 14, 2018.
Li, J. et al., "BIN2, a New Brassinosteroid-Insensitive Locus in *Arabidopsis*", Plant Physiology, vol. 127, No. 1, pp. 14-22, Sep. 2001.
Voytas, D. F., "Plant Genome Engineering with Sequence-Specific Nucleases", Annual Review of Plant Biology, 64(1), pp. 327-350. doi:10.1146/annurev-arplant-042811-105552, 2013.
Khaoula Belhaj et al., "Plant genome editing made easy: targeted mutagenesis in model and crop plants using the CRISPR/Cas system". Plant Methods, 9(1), 39. doi:10.1186/1746-4811-9-39, 2013.
Ye Huaxun et al., "Recent Advances in the Regulation of Brassinosteroid Signaling and Biosynthesis Pathways", Journal of integrative Plant Biology, 53(6), pp. 455-468. doi:10.1111/j.1744-7909.2011,01046. x, 2011.
Kanchiswamy C N et al., "Non-GMO genetically edited crop plants", Trends in Biotechnology, 33(9), pp. 489-491, doi:10.1016/j.tibtech.2015.04.002, 2015.
Office Action of BR Patent Application No. BR 11 2018 007061 0, dated Mar. 3, 2020.
EPO, Office Action of EP. 16 853 921.1 dated Sep. 7, Sep. 7, 2020.
JPO, Office Action of JP 2019-164233 dated Oct. 1, 2020.

\* cited by examiner

[Fig. 1a]
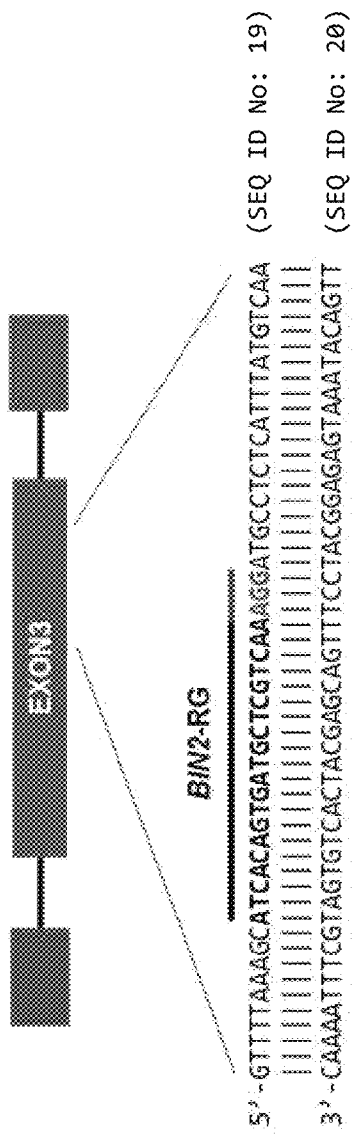
[Fig. 1b]
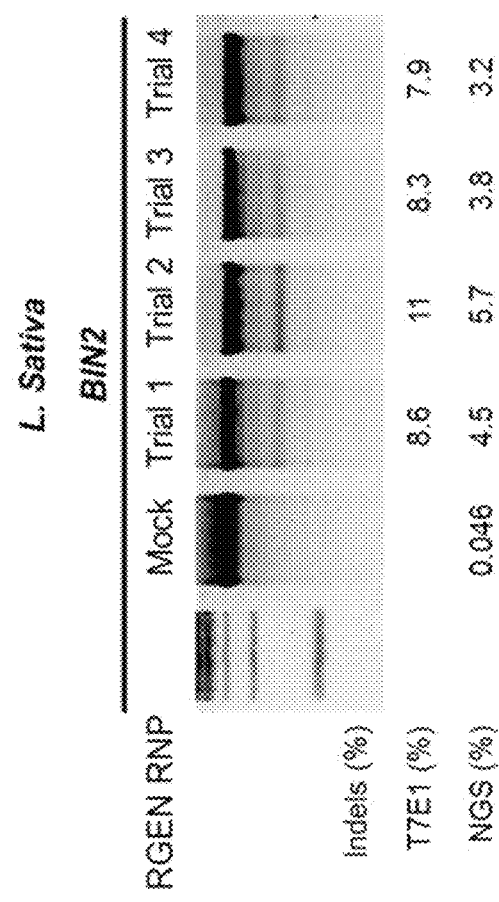

[Fig. 1c]

Trial 1

Mutated locus

```
                    PAM
ATCACAGTGATGATGCTCGT-CAAAGG (SEQ ID No: 21)  WT
ATCACAGTGATGATGCTCGTCCAAAGG (SEQ ID No: 22)  + 1bp (3.1%)
ATCACAGTGATGATGCTCG--CAAAGG (SEQ ID No: 23)  - 1bp (0.26%)
ATCACAGTGATGATGCTCGTACAAAGG (SEQ ID No: 24)  + 1bp (0.25%)
ATCACAGTGATGATGCTCGTGCAAAGG (SEQ ID No: 25)  + 1bp (0.21%)
```

Trial 2

Mutated locus

```
                    PAM
ATCACAGTGATGATGCTCGT-CAAAGG (SEQ ID No: 26)  WT
ATCACAGTGATGATGCTCGTCCAAAGG (SEQ ID No: 27)  + 1bp (3.3%)
ATCACAGTGATGATGCT----CAAAGG (SEQ ID No: 28)  - 3bp (0.68%)
ATCACAGTGATGATGCTCGTACAAAGG (SEQ ID No: 29)  + 1bp (0.37%)
ATCACAGTGATGATGCTCGTGCAAAGG (SEQ ID No: 30)  + 1bp (0.26%)
```

Trial 3

Mutated locus

```
                    PAM
ATCACAGTGATGATGCTCGT-CAAAGG (SEQ ID No: 31)  WT
ATCACAGTGATGATGCTCGTTCAAAGG (SEQ ID No: 32)  + 1bp (2.4%)
ATCACAGTGATGATGCTCGTACAAAGG (SEQ ID No: 33)  + 1bp (0.43%)
ATCACAGTGATGATGCTCGTGCAAAGG (SEQ ID No: 34)  + 1bp (0.27%)
ATCACAGTGATGATGCTCGTCCAAAGG (SEQ ID No: 35)  + 1bp (0.15%)
```

Trial 4

Mutated locus

```
                    PAM
ATCACAGTGATGATGCTCGT-CAAAGG (SEQ ID No: 36)  WT
ATCACAGTGATGATGCTCGTTCAAAGG (SEQ ID No: 37)  + 1bp (2.2%)
ATCACAGTGATGATGCTCGTACAAAGG (SEQ ID No: 38)  + 1bp (0.27%)
ATCACAGTGATGATGCT---CAAAGG  (SEQ ID No: 39)  - 3bp (0.20%)
ATCACAGTGATGATGCTCGTGCAAAGG (SEQ ID No: 40)  + 1bp (0.11%)
```

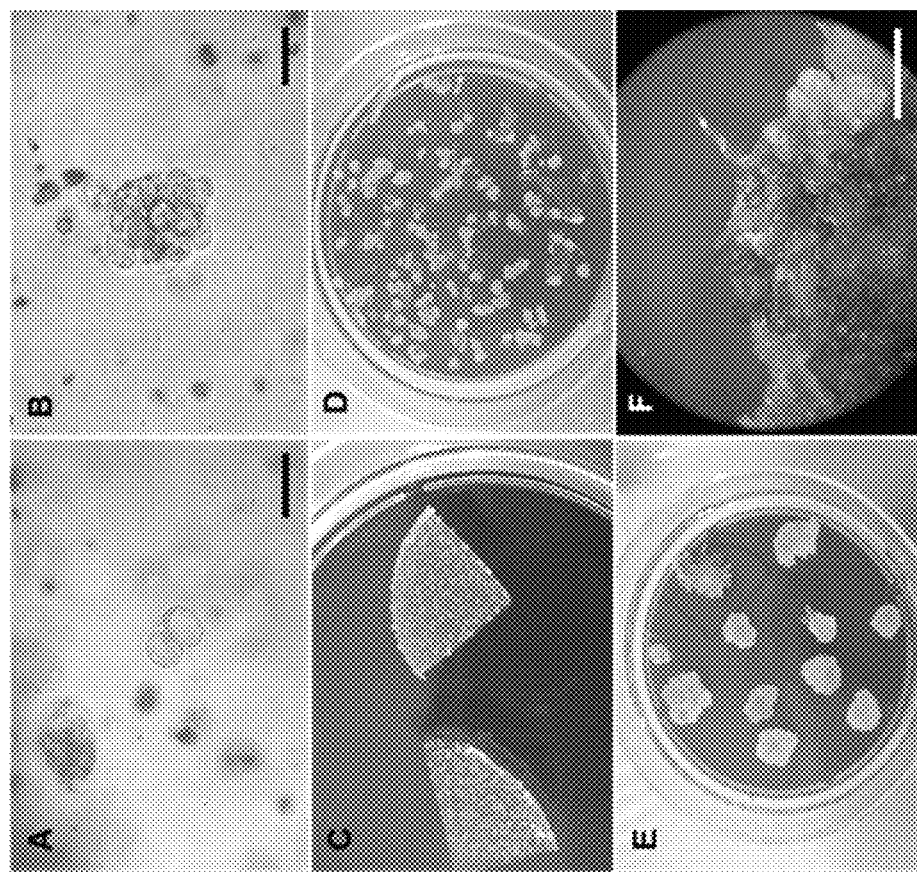
[Fig. 2]

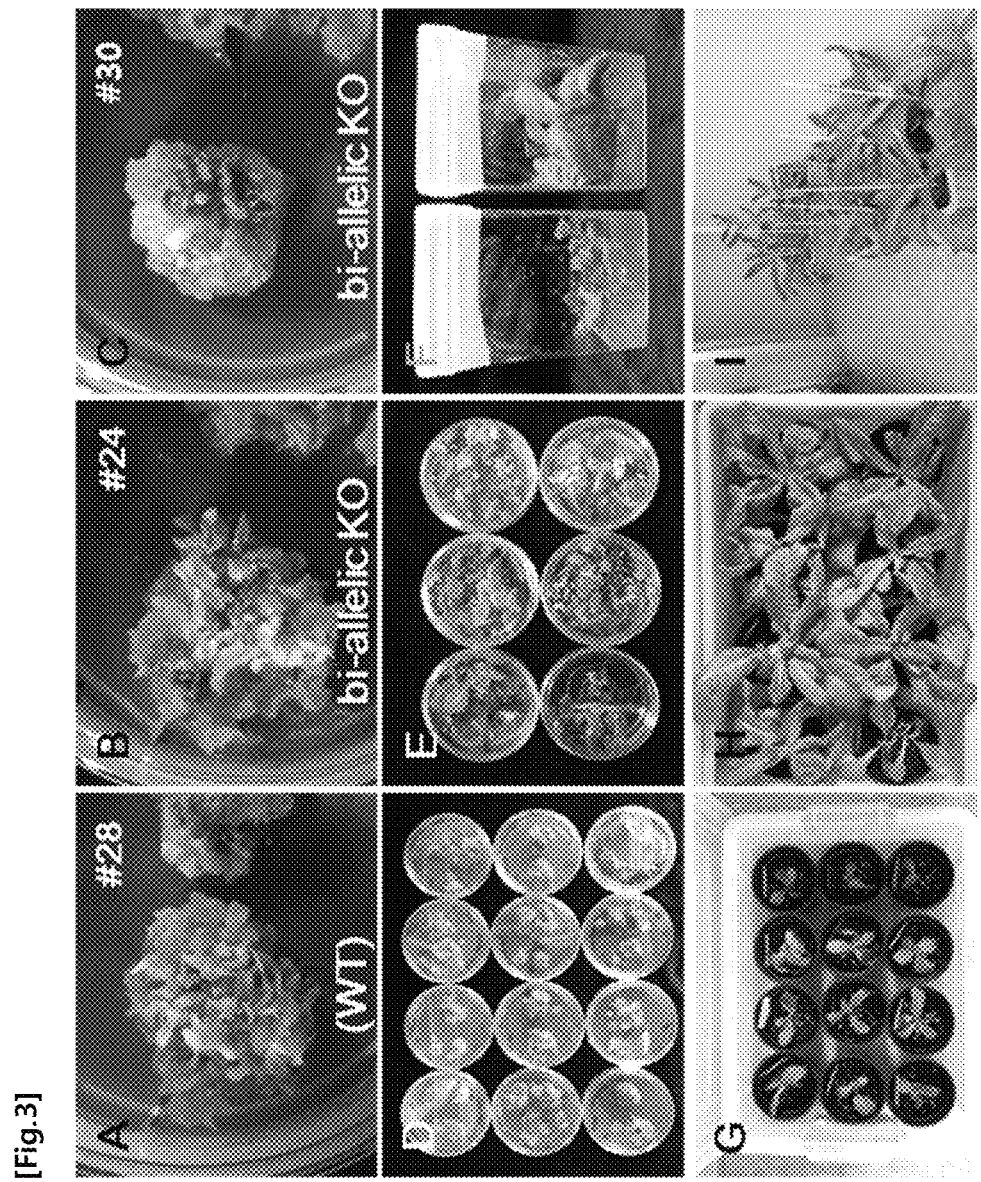
[Fig.3]

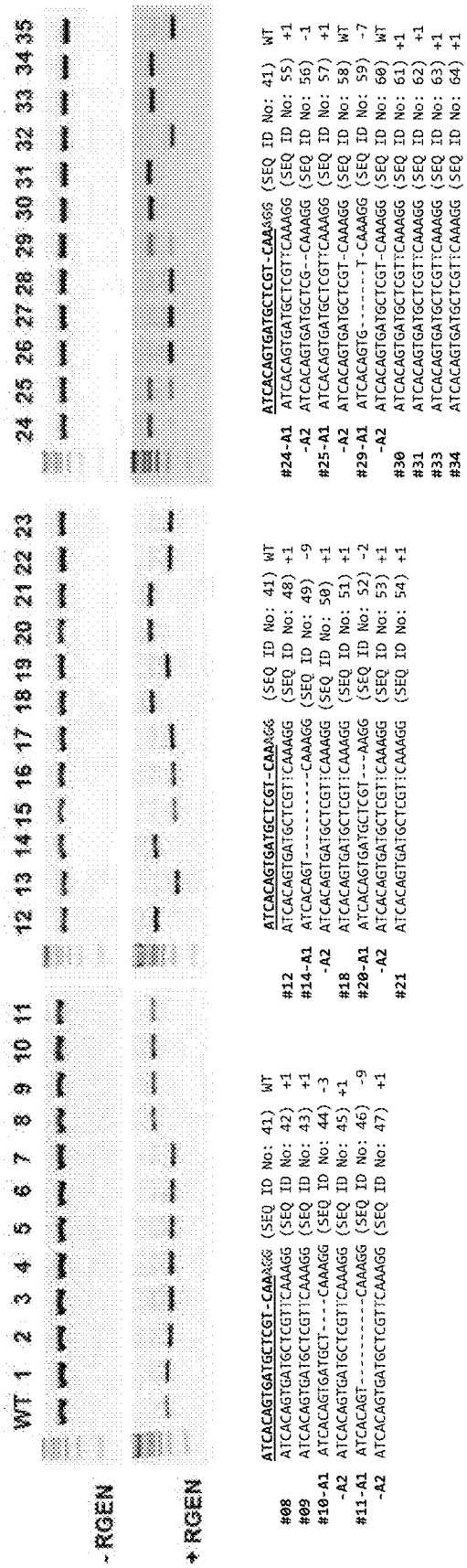

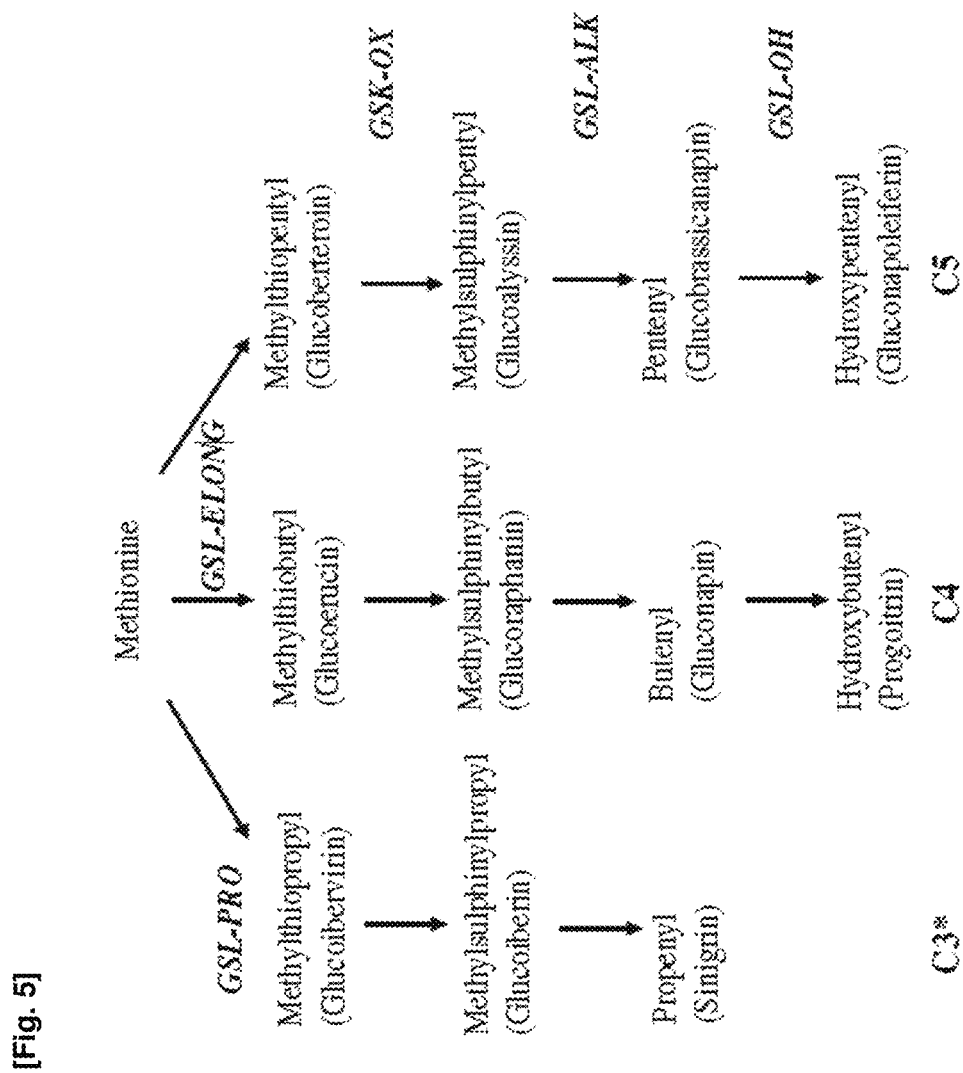
[Fig. 5]

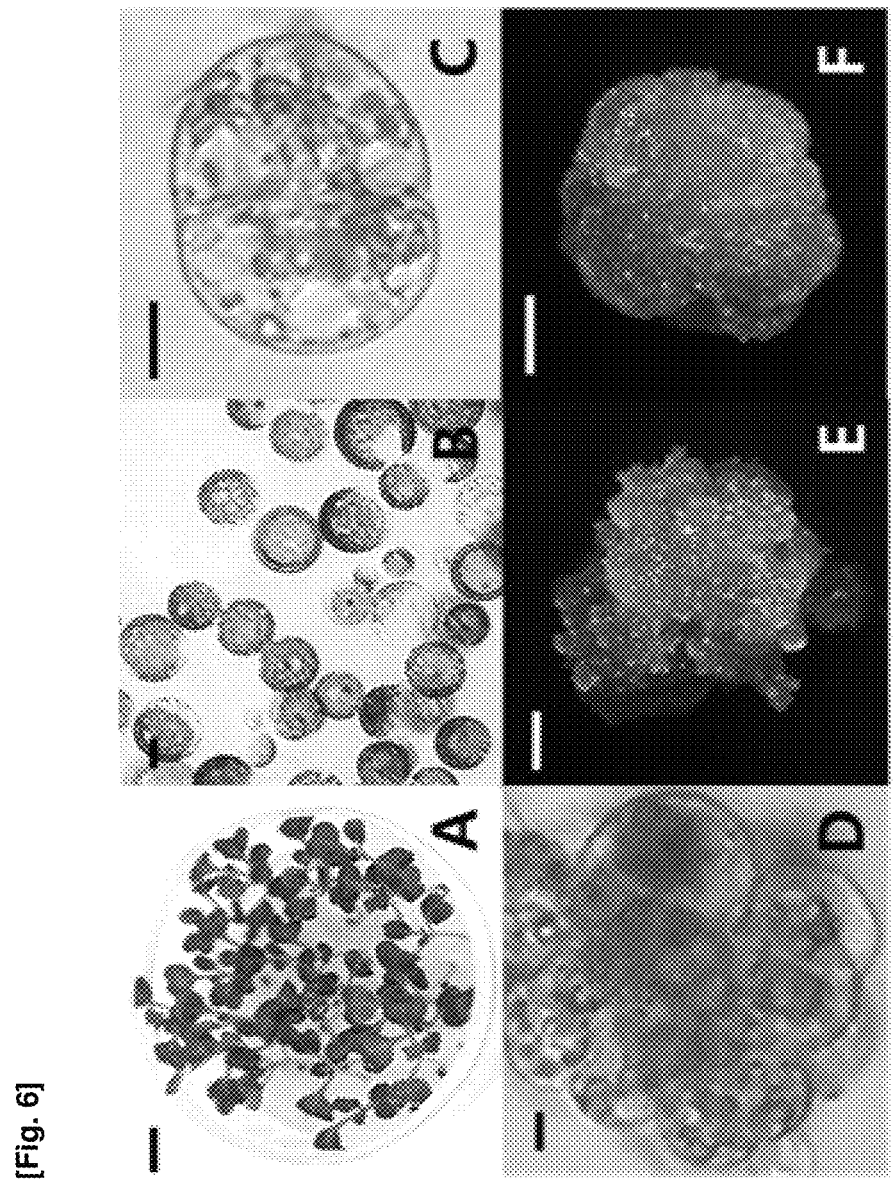
[Fig. 6]

SEQUENCE LISTING

<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: Synthetic (LsBin2-deepF)

<400> SEQUENCE: 1
tagaaacggg ggaaactgtg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic (LsBin2-deepR)

<400> SEQUENCE: 2
cccaaaagaa gctcagcaag                                              20

<210> SEQ ID NO 3

```
<211> LENGTH: 20
<212> TYPE: DNA
<213> ORGANISM: Artificial Sequence
<220> FEATURE:
<223> OTHER INFORMATION: Synthetic (BoGSL-ALK F1_1-5)

<400> SEQUENCE: 3
gcgaaaagaa tgggtgcaga                                             20

<210> SEQ ID NO 4
<211> LENGTH: 21
<212> TYPE: DNA
<213> ORGANISM: Artificial Sequence
<220> FEATURE:
<223> OTHER INFORMATION: Synthetic (BoGSL-ALK R1_1-5)

<400> SEQUENCE: 4
tggcatccaa aactgacttc t                                           21

<210> SEQ ID NO 5
<211> LENGTH: 20
<212> TYPE: DNA
<213> ORGANISM: Artificial Sequence
<220> FEATURE:
<223> OTHER INFORMATION: Synthetic (BoGSL-ALK F2_6-9)

<400> SEQUENCE: 5
tcgagttacc agttgaggct                                             20

<210> SEQ ID NO 6
<211> LENGTH: 23
<212> TYPE: DNA
<213> ORGANISM: Artificial Sequence
<220> FEATURE:
<223> OTHER INFORMATION: Synthetic (BoGSL-ALK R2_6-9)

<400> SEQUENCE: 6
cgacatgacg ttacctcata gtc                                         23

<210> SEQ ID NO 7
<211> LENGTH: 20
<212> TYPE: DNA
<213> ORGANISM: Artificial Sequence
<220> FEATURE:
<223> OTHER INFORMATION: Synthetic (BoGSL-ALK F3_10-12)

<400> SEQUENCE: 7
cagcgaaacg atccagaagt                                             20

<210> SEQ ID NO 8
<211> LENGTH: 21
<212> TYPE: DNA
<213> ORGANISM: Artificial Sequence
<220> FEATURE:
<223> OTHER INFORMATION: Synthetic (BoGSL-ALK R3_10-12)

<400> SEQUENCE: 8
ctgaccgcaa cattagcatc a                                           21

<210> SEQ ID NO 9
<211> LENGTH: 20
<212> TYPE: DNA
<213> ORGANISM: Artificial Sequence
<220> FEATURE:
<223> OTHER INFORMATION: Synthetic (BoGSL-ALK F4 13-15)

<400> SEQUENCE: 9
```

```
gcgcagatga tgaggagaag                                              20

<210> SEQ ID NO 10
<211> LENGTH: 22
<212> TYPE: DNA
<213> ORGANISM: Artificial Sequence
<220> FEATURE:
<223> OTHER INFORMATION: Synthetic (BoGSL-ALK R4 13-15)

<400> SEQUENCE: 10
agaatctcca gccataacaa cg                                           22

<210> SEQ ID NO 11
<211> LENGTH: 20
<212> TYPE: DNA
<213> ORGANISM: Artificial Sequence
<220> FEATURE:
<223> OTHER INFORMATION: Synthetic (BIN2 target site)

<400> SEQUENCE: 11
atcacagtga tgctcgtcaa                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic (BoGSL-ALK 1)

<400> SEQUENCE: 12
acttccagtc atctatctct                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic (BoGSL-ALK 2)

<400> SEQUENCE: 13
tggtccgaga gatagatgac                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic (BoGSL-ALK 7)

<400> SEQUENCE: 14
ctgctacgcc ctgattgtga                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic (BoGSL-ALK 9)

<400> SEQUENCE: 15
gtcttgttac cctcacaatc                                              20

<210> SEQ ID NO 16
<211> LENGTH: 20
<212> TYPE: DNA
```

```
<213> ORGANISM: Artificial Sequence
<220> FEATURE:
<223> OTHER INFORMATION: Synthetic (BoGSL-ALK 12)

<400> SEQUENCE: 16
agaatggtca tagagagctt                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic (BoGSL-ALK 13)

<400> SEQUENCE: 17
atatgagatt gaaggtttgg                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic (BoGSL-ALK 15)

<400> SEQUENCE: 18
acaacgaaag agttatgaga                                                    20

<210> SEQ ID NO 19
<211> LENGTH: 53
<212> TYPE: DNA
<213> ORGANISM: Artificial Sequence
<220> FEATURE:
<223> OTHER INFORMATION: Synthetic Sequence

<400> SEQUENCE: 19
gttttaaagc atcacagtga tgctcgtcaa aggatgcctc tcatttatgt caa              53

<210> SEQ ID NO 20
<211> LENGTH: 53
<212> TYPE: DNA
<213> ORGANISM: Artificial Sequence
<220> FEATURE:
<223> OTHER INFORMATION: Synthetic Sequence

<400> SEQUENCE: 20
caaaatttcg tagtgtcact acgagcagtt cctacggag agtaaataca gtt               53

<210> SEQ ID NO 21
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 21
atcacagtga tgctcgtcaa agg                                                23

<210> SEQ ID NO 22
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 22
atcacagtga tgctcgtcca aagg                                               24
```

```
<210> SEQ ID NO 23
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 23
atcacagtga tgctcgcaaa gg                                                 22

<210> SEQ ID NO 24
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 24
atcacagtga tgctcgtaca aagg                                               24

<210> SEQ ID NO 25
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 25
atcacagtga tgctcgtgca aagg                                               24

<210> SEQ ID NO 26
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 26
atcacagtga tgctcgtcaa agg                                                23

<210> SEQ ID NO 27
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 27
atcacagtga tgctcgtcca aagg                                               24

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 28
atcacagtga tgctcaaagg                                                    20

<210> SEQ ID NO 29
<211> LENGTH: 24
<212> TYPE: DNA
<213> ORGANISM: Artificial Sequence
<220> FEATURE:
```

```
<223> OTHER INFORMATION: Synthetic Sequence

<400> SEQUENCE: 29
atcacagtga tgctcgtaca aagg                                              24

<210> SEQ ID NO 30
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 30
atcacagtga tgctcgtgca aagg                                              24

<210> SEQ ID NO 31
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 31
atcacagtga tgctcgtcaa agg                                               23

<210> SEQ ID NO 32
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 32
atcacagtga tgctcgttca aagg                                              24

<210> SEQ ID NO 33
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 33
atcacagtga tgctcgtaca aagg                                              24

<210> SEQ ID NO 34
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 34
atcacagtga tgctcgtgca aagg                                              24

<210> SEQ ID NO 35
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 35
atcacagtga tgctcgtcca aagg                                              24
```

```
<210> SEQ ID NO 36
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 36
atcacagtga tgctcgtcaa agg                                              23

<210> SEQ ID NO 37
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 37
atcacagtga tgctcgttca aagg                                             24

<210> SEQ ID NO 38
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 38
atcacagtga tgctcgtaca aagg                                             24

<210> SEQ ID NO 39
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 39
atcacagtga tgctcaaagg                                                  20

<210> SEQ ID NO 40
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 40
atcacagtga tgctcgtgca aagg                                             24

<210> SEQ ID NO 41
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 41
atcacagtga tgctcgtcaa agg                                              23

<210> SEQ ID NO 42
<211> LENGTH: 24
<212> TYPE: DNA
<213> ORGANISM: Artificial Sequence
<220> FEATURE:
<223> OTHER INFORMATION: Synthetic Sequence
```

```
<400> SEQUENCE: 42
atcacagtga tgctcgtcca aagg                                         24

<210> SEQ ID NO 43
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 43
atcacagtga tgctcgttca aagg                                         24

<210> SEQ ID NO 44
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 44
atcacagtga tgctcaaagg                                              20

<210> SEQ ID NO 45
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 45
atcacagtga tgctcgttca aagg                                         24

<210> SEQ ID NO 46
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 46
atcacagtca aagg                                                    14

<210> SEQ ID NO 47
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 47
atcacagtga tgctcgttca aagg                                         24

<210> SEQ ID NO 48
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 48
atcacagtga tgctcgttca aagg                                         24

<210> SEQ ID NO 49
<211> LENGTH: 14
```

```
<212> TYPE: DNA
<213> ORGANISM: Artificial Sequence
<220> FEATURE:
<223> OTHER INFORMATION: Synthetic Sequence

<400> SEQUENCE: 49
atcacagtca aagg                                                        14

<210> SEQ ID NO 50
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 50
atcacagtga tgctcgttca aagg                                             24

<210> SEQ ID NO 51
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 51
atcacagtga tgctcgttca aagg                                             24

<210> SEQ ID NO 52
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 52
atcacagtga tgctccaaag g                                                21

<210> SEQ ID NO 53
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 53
atcacagtga tgctcgttca aagg                                             24

<210> SEQ ID NO 54
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 54
atcacagtga tgctcgttca aagg                                             24

<210> SEQ ID NO 55
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 55
```

```
atcacagtga tgctcgttca aagg                                           24
```

<210> SEQ ID NO 56
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 56

```
atcacagtga tgctcgcaaa gg                                             22
```

<210> SEQ ID NO 57
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 57

```
atcacagtga tgctcgttca aagg                                           24
```

<210> SEQ ID NO 58
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 58

```
atcacagtga tgctcgtcaa agg                                            23
```

<210> SEQ ID NO 59
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 59

```
atcacagtgt caaagg                                                    16
```

<210> SEQ ID NO 60
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 60

```
atcacagtga tgctcgtcaa agg                                            23
```

<210> SEQ ID NO 61
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 61

```
atcacagtga tgctcgttca aagg                                           24
```

<210> SEQ ID NO 62
<211> LENGTH: 24
<212> TYPE: DNA
<213> ORGANISM: Artificial Sequence

```
<220> FEATURE:
<223> OTHER INFORMATION: Synthetic Sequence

<400> SEQUENCE: 62
atcacagtga tgctcgttca aagg                                              24

<210> SEQ ID NO 63
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 63
atcacagtga tgctcgttca aagg                                              24

<210> SEQ ID NO 64
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 64
atcacagtga tgctcgttca aagg                                              24
```

METHOD FOR PRODUCING GENOME-MODIFIED PLANTS FROM PLANT PROTOPLASTS AT HIGH EFFICIENCY

TECHNICAL FIELD

The present invention relates to a method of increasing the production efficiency of genome-edited plants, regenerated from plant protoplasts, by introducing a Cas protein and a a guide RNA into the plant protoplasts.

BACKGROUND ART

It remains unclear whether the genome-edited plants will be regulated under genetically-modified organism (GMO) legislation passed by the EU, and other countries (Jones, H. D., Nature Plants, 2015, 1: 14011). Molecular scissors (programmable nucleases) induce small insertions and deletions (indel) or substitutions to chromosomal target sites that are indistinguishable from naturally occurring genetic variation. Such genome-edited plants may be considered GMOs in certain countries, hampering the widespread use of programmable nucleases in plant biotechnology and agriculture. For example, when *Agrobacterium* is used, genome-edited plants produced thereby have foreign DNA sequences, including the genes of encoded programmable nucleases in the genome. Removal of these *Agrobacterium*-derived DNA sequences by breeding is not feasible in asexually-reproducing plants such as the grape, potato, or banana.

Alternatively, non-integrating plasmids that encode programmable nucleases can be transfected into plant cells such as protoplasts. However, the present inventors paid attention to the fact that transfected plasmids are degraded in cells via endogenous nucleases and that the resulting small DNA fragments can be inserted into the Cas9 on-target and off-target sites, as exemplified in human cells (Kim, S, etc., Genome research, 2014, 24: 1012-1019).

Delivery of the preassembled Cas9 protein-gRNA ribonucleoproteins (RNPs), rather than plasmids encoding Cas9 protein, and gRNA into plant cells could avert the possibility of inserting recombinant DNA into the host genome. Furthermore, as shown in human cells, RNA-guided engineered nuclease (RGEN) RNPs cleave chromosomal target sites immediately after transfection and are degraded rapidly by endogenous proteases in cells, with the potential to reduce mosaicism, and off-target effects in regenerated whole plants. Preassembled RGEN RNPs can be used in a number of applications across plant species, absent prior optimization of codon usage, as well as promoters to express Cas9 and gRNAs in each species. In addition, RGEN RNPs enable pre-screening in vitro to select highly active gRNAs, and the genotyping of mutant clones via restriction fragment length polymorphism (RFLP) analysis. However, there have been no reports that indicate that RGEN RNPs were introduced into plant protoplasts with the effect of confirming genome editing, and that plants successfully regenerated from the protoplasts.

DISCLOSURE OF INVENTION

Technical Problem

The present inventors have made extensive efforts to develop present technology capable of editing the genome of plants by applying Cas protein-gRNA RNP to the plants. It is found that a genome-edited plant can be produced with a high efficiency by introducing a Cas protein and a guide RNA into an isolated plant protoplast to edit the genome of the plant protoplast and regenerate the plant protoplast, thereby completing the present invention.

Technical Solution

The present disclosure provides a method for increasing the production efficiency of a genome-edited plant from a plant protoplast, comprising the steps of: (i) editing a genome of a plant protoplast by introducing a Cas protein and a guide RNA into an isolated plant protoplast; and (ii) producing a genome-edited plant by regenerating the plant protoplast.

Another aspect of the present invention is to provide a plant regenerated from the genome-edited plant protoplast produced by the above method.

Still another aspect of the present invention is to provide a composition for increasing the production efficiency of a genome-edited plant from a plant protoplast comprising a Cas protein and a guide RNA specific for DNA encoding a target gene.

Advantageous Effects

According to the various aspects of the present invention, the method of increasing the production efficiency of gene-edited plants makes it possible to efficiently produce target gene-mutated plants and to minimize the insertion of a foreign DNA into plants. Thus, by way of example, the present invention can be very advantageously used in a wide variety of fields, including the agriculture, food and biotechnology.

BRIEF DESCRIPTION OF THE DRAWINGS

FIG. 1 shows Cas9 protein-guide RNA ribonucleoprotein (RNP)-mediated gene disruption in lettuce protoplasts. (a) The target sequence in BRASSINOSTEROID INSENSITIVE 2(BIN2) gene; (b) Mutation frequencies measured by the T7E1 assay and targeted deep sequencing in bulk population; (c) Mutant DNA sequences induced by Cas9 protein-guide RNA ribonucleoprotein (RNP) in lettuce. The protospacer-adjacent motif (PAM) sequences are shown in red. Inserted nucleotides are shown in blue. WT: wild-type.

FIG. 2 shows protoplast division and in vitro redifferentiation after editing of lettuce genes by a direct introduction of RGEN RNP.

FIG. 3 shows a redifferentiation process for obtaining a target gene (Lsbin2)-edited lettuce plant.

FIG. 4 shows genetic analysis of lettuce microcalli derived from a single protoplast treated with Cas9 protein-guide RNA. (a) Genotyping of microcalli. (Top) RGEN RFLP analysis. (Bottom) DNA variant sequences in microcalli. (b) Summary of genetic variation analysis of BIN2 gene in TO generation.

FIG. 5 shows the glucosinolate biosynthesis pathway in *B. napus* based on genetic analysis.

FIG. 6 shows callus formation after transfection of Cas9 protein-guide RNA RNP into cotyledon-derived protoplasts of *Brassica oleracea*. (A) Cotyledons of *Brassica oleracea* seedlings; (B) isolated protoplasts; (C) First cell division after 3 to 5 days of protoplast culture; (D) Protoplasts in 2 to 3 weeks of culture after transfection with Cas9 protein-guide RNA RNP; and (E and F) Micro-callus formation after 9 to 11 weeks of culture. Scale bar: 1 cm (A), 10 μm (B to D), and 1 mm (E and F).

BEST MODE FOR CARRYING OUT THE INVENTION

Genome editing methods such as zinc finger nuclease (ZFN), transcription activator-like effector DNA binding protein (TALLEN) and clustered regularly interspaced short palindromic repeats (CRISPR)/Cas system are very useful methods capable of inducing targeted mutations, but the use thereof in plants is limited due to issues regarding GMOs (genetically modified organisms). Accordingly, the present inventors have made efforts to develop a method capable of producing genome-edited plants without inserting foreign DNA sequences. They found that when a Cas protein and a guide RNA are introduced into plant protoplasts to edit the genome of the plant protoplasts, the genomes of the plants produced by regenerating the genome-edited protoplasts are edited at significantly high frequencies regardless of target genes. Thus, the present invention provides a method of increasing the production efficiency of genome-edited plants, regenerated from plant protoplasts, by introducing a Cas9 protein and a guide RNA into the plant protoplasts.

This will be described in detail hereinafter. In the meantime, each of the description and the embodiments disclosed herein may be applied to other description and embodiments. In other words, any combination of various elements disclosed in the present invention falls within the scope of the present invention. In addition, the scope of the present invention should not be construed to be limited by the specific description or embodiments described below.

One aspect of the present invention is directed to a method for increasing the production efficiency of a genome-edited plant a plant protoplast comprising the steps of: (i) editing a genome of a plant protoplast by introducing a Cas protein and a guide RNA into an isolated plant protoplast; and (ii) producing a genome-edited plant by regenerating the plant protoplast.

As used herein, the term "genome editing" or "genome editing technology" refers to one or more techniques capable of introducing a targeted variation and/or mutation into the nucleotide sequence of a genome in animal and/or plant cells, including human cells, and means of knocking-out or knocking-in a specific gene, or introducing a variation into a non-coding DNA sequence that produces no protein. For the purpose of the present disclosure, the genome editing may mean introducing a mutation or change into a plant using particularly a Cas protein and a guide RNA. The method of the present invention can remarkably increase the production efficiency of a genome-edited plant from a plant protoplast.

Hereinafter, each step of the method will be described in detail.

Step (i) is a step of editing a genome of a plant protoplast by introducing a Cas protein or a guide RNA into an isolated plant protoplast. In step (i), a Cas protein and a guide RNA specific for the DNA encoding a target gene are introduced into a plant protoplast, whereby the plant protoplast can be transfected within a short time while minimizing the chance of inserting foreign DNA into the genome.

As used herein, the term "Cas protein" means a major protein component of the CRISPR/Cas system and is a protein that can act as an activated endonuclease. The Cas protein corresponds to a gene scissors (or sometimes referred herein as "a molecular scissor") named RNA-guided engineered nuclease (RGEN). The Cas protein may form a complex with a CRISPR RNA (crRNA) and a trans-activating crRNA (tracrRNA) to exhibit the activity thereof.

The Cas protein recognizes a specific nucleotide sequence in the genome and causes double strand breaks (DSBs). The double strand breaks include cleaving the double strands of DNA to make a blunt end or a cohesive end. DSBs are efficiently repaired by the homologous recombination or non-homologous end-joining (NHEJ) mechanism in cells, during which a desired mutation can be introduced into a target site. In the present disclosure, the Cas protein may recognize NGG trinucleotide, but is not limited thereto.

Information on Cas protein or a gene is available from known databases such as GenBank of National Center for Biotechnology Information (NCBI). Specifically, the Cas protein may be a Cas9 protein or a variant thereof. In addition, the Cas protein may be a Cas protein derived from *Streptococcus* sp, *Neisseria* sp., *Pasteurella* sp, *Francisella* sp, and *Campylobacter* sp, but is not limited thereto. More specifically, the Cas protein may be derived from *Streptococcus pyogenes*. However, the present invention is not limited to the above described examples.

A variant of the Cas9 protein may be in a mutant form of Cas9 protein in which the catalytic aspartate residue is substituted with another amino acid, for example, alanine, but is not limited thereto.

Furthermore, the Cas protein in the present disclosure may be a recombinant protein. The term "recombinant" when used herein with reference, e.g., to a cell, nucleic acid, protein, or vector, indicates that the cell, nucleic acid, protein or vector, has been modified by an introduction of a heterologous nucleic acid or protein or alteration of a native nucleic acid or protein, or that the cell is modified by being derived from a modified cell. Thus, for example, a recombinant Cas9 protein can be generated by reconstituting a Cas9 protein-encoding sequence using a human codon table.

The Cas protein may be in a form that enables the protein to act in the nucleus, or in a form that is easily introduced into a cell. For example, the Cas protein may be linked to a cell-penetrating peptide or a protein transduction domain. The protein transduction domain may be poly-arginine or an HIV-derived TAT protein, but it is not limited thereto. As a cell-penetrating peptide or a protein transduction domain, various kinds of cell-penetrating peptides or protein transduction domains are well-known in the art besides the above-described example, and thus a person skilled in the art may apply various examples to the present invention without any limitations.

As used herein, the term "guide RNA" means a RNA specific for a DNA encoding a target gene or sequence. The guide RNA may bind complementarily to the whole or a portion of the target sequence so that the Cas protein can cleave the target sequence.

Generally, the term "guide RNA" may also refers to a dual RNA comprising two RNAs, that is, CRISPR RNA (crRNA) and trans-activating crRNA (tracrRNA). Alternatively, the guide RNA may refer to a single-chain or single guide RNA (sgRNA) comprising a first region comprising a sequence which is entirely or partially complementary to a target DNA sequence, and a second region comprising a sequence that interacts with RNA-guided nuclease, but any form of guide RNA that enables RNA-guided nuclease to be active in the target sequence may be included in the scope of the present disclosure without any limitations. For example, when the guide RNA is applied to Cas9, it may be in the form of a dual RNA comprising crRNA and tracrRNA, or may be in the form of a single guide RNA (sgRNA) wherein the major regions of crRNA and tracrRNA are fused to each other. The sgRNA may comprise a region complementary to a target DNA sequence (herein termed as a "spacer region", "target DNA recognition sequence", "base pairing region", etc.), and a hairpin structure for binding to the Cas protein. More particularly, the sgRNA may comprise a region having a sequence entirely or partially complementary to a target DNA sequence, a hairpin structure for binding to the Cas protein, and a terminator sequence. These elements may be sequentially arranged in the 5' to 3' direction. However, the scope of the present disclosure is not limited thereto, and any form of a guide RNA may also be used in the present invention, as long as it comprises a region complementary to the whole or a portion of a target DNA or a major region of crRNA.

The guide RNA may be in the form of naked RNA, but is not limited thereto. When a guide RNA is to be transfected into a cell or an organism in the form of naked RNA, the guide RNA can be prepared using any in vitro transcription system known in the art.

The guide RNA or sgRNA may comprise a sequence entirely or partially complementary to a target DNA sequence, and may comprise one or more additional nucleotides at the upstream of sgRNA, particularly the 5' end of the sgRNA. The additional nucleotides may include guanine (G), but are not limited thereto.

The present disclosure may be characterized by introducing a Cas protein and a guide RNA directly into a protoplast without using an intracellular expression system such as a vector system. This can minimize the introduction of one or more foreign DNAs into plants, thereby addressing concerns about GMOs. In an aspect, the Cas protein and the guide RNA may be prepared in a preassembled form (i.e., a ribonucleoprotein (RNP) form) before the introduction of the preassembled form into a protoplast, but are not limited thereto. In the present disclosure, Cas protein-guide RNA RNP and RGEN-RNP may be used in the same sense.

As used herein, the term "target gene" means some genes in the plant genome to be edited by the present disclosure. Namely, principally, the target gene is not limited to a particular kind of gene, and may comprise both a coding region and a non-coding region. A person skilled in the art can select the target gene according to a desired variation for the genome-edited plant to be produced. The target gene may be Brassinosteroid Insensitive 2 (BIN2) gene or Glucosinolate-oxoglutarate-dependent dioxygenase homolog (GSL-ALK), but is not limited thereto.

In step (i), the introduction of a Cas protein or a guide RNA into the plant protoplast may be performed by various methods known in the art, such as a microinjection, electroporation, DEAE-dextran treatment, lipofection, nanoparticle-mediated transfection, protein transduction domain-mediated transduction, and PEG-mediated transfection so that the Cas protein or the guide RNA can be delivered into a cell, but is not limited thereto. The Cas protein may be delivered into a cell in a form complexed with the guide RNA or in an independent form.

The introduction may be performed by co-transfection or serial-transfection. The serial-transfection may be performed by first transfecting the Cas protein, and then transfecting a naked guide RNA, but is not limited thereto.

In the present disclosure, a plant that can be used for obtaining the plant protoplast is not particularly limited to its derivation, but the plant protoplast may be derived from *Lactuca sativa* or *Brassica oleracea*.

Step (ii) is a step of producing a genome-edited plant by regenerating the plant protoplast whose genome is edited, and may comprise, but not limited to, the steps of: forming a callus by culturing the plant protoplast; and producing a regenerated plant by further culturing the callus.

Medium compositions that used in the steps of forming the callus and of producing the regenerated plant from the callus may be properly selected by a person skilled in the art, depending on the kind and status of plant. Conditions for such culture are known in the art.

Specifically, in order to induce callus formation from the genome-edited protoplast, the callus may be cultured in a callus induction medium containing MS salt, 6% myo-inositol, 0.4 mg/L thiamine-HCl, 2 mg/L 2,4-D, 0.5 mg/L BA and 30% sucrose. Micro-calli obtained from the culture may be further cultured in a callus induction solid medium containing MS salt, 0.6% myo-inositol, 0.4 mg/L thiamine-HCl, 2 mg/L 2,4-D, 0.5 mg/L BA, 3 mg/L $AgNO_3$, 3% sucrose and 0.4% gelrite, thereby producing green plantlets, and the plantlets may be transferred to MS basal medium to induce root production, but the scope of the present invention is not limited thereto. In addition, a person skilled in the art can suitably control external environmental conditions such as temperature and light/dark conditions depending on the kind and status of plant.

In a specific example of the present invention, a RNP targeting brassinosteroid intensive 2(BIN2) gene was introduced into protoplasts isolated from lettuce, and then the genome-edited protoplasts were regenerated. As a result, it was shown that the completely regenerated plant showed a genome editing efficiency of 46%, which is about ten (10)-fold higher than the editing frequency of the protoplasts (FIGS. 1b and 4b). Furthermore, when the glucosinolate-oxoglutarate-dependent dioxygenase homolog (GSL-ALK) gene in protoplasts isolated from *Brassica oleracea* was disrupted, like the case of lettuce, it was shown that the genome editing efficiency was not high (0.0% to 1%) in the protoplasts introduced with the RNP, but was significantly increased (24.0% to 100%) in the calli regenerated from the protoplasts (Tables 2 and 3). From the above-described results, it could be seen that the cell proliferation and growth rates of RNP-introduced protoplasts in the regeneration process are increased compared to protoplasts not introduced with the RNP, and thus the protoplasts are regenerated into plants.

Another aspect of the present disclosure is directed to a plant regenerated from the genome-edited plant protoplast produced by the above method.

Still another aspect of the present disclosure is directed to a composition for increasing the production efficiency of a genome-edited plant from a plant protoplast, comprising a Cas protein and a guide RNA specific for a DNA encoding a target gene.

The guide RNA, the Cas protein, genome editing of the plant protoplast, and the plant regenerated from the protoplast are as described above. The genome-edited plant has a mutation caused by a targeted mutation based on the composition of the present invention. The mutation may be any one of deletion, insertion, translocation and inversion. The position of the mutation may depend on the sequence of a guide RNA of the composition.

The target gene may be a Brassinosteroid Insensitive 2 (BIN2) gene or a Glucosinolate-oxoglutarate-dependent dioxygenase homolog (GSL-ALK) gene, but is not limited thereto.

BEST MODE FOR INVENTION

EXAMPLES

Hereinafter, the present disclosure will be described in further detail with reference to examples. It will be obvious to a person having ordinary skill in the art that these examples are for illustrative purposes only and are not to be construed to limit the scope of the present invention.

Example 1: Isolation of Plant Protoplasts

To isolate lettuce protoplasts, lettuce (*Lactuca sativa* L.) Cheongchima seeds were sterilized in a solution containing 70% ethanol and 0.4% hypochlorite for 15 min, washed three times with distilled water, and cultured on ½×M/S solid medium supplemented with 2% sucrose. The culture was performed by growing in a growth room under a 16-hr light (150 µmol m$^{-2}$ s$^{-1}$) and 8-hr dark cycle at 25° C. At 7 days of culture, the cotyledons of lettuce seedlings were digested with an enzyme solution (1.0% cellulase R10, 0.5% macerozyme R10, 0.45 M mannitol, 20 mM MES [pH 5.7], CPW solution) by shaking incubation (40 rpm) for 12 hours at 25° C. in darkness, and then diluted with an equal volume of W5 solution. The diluted solution was filtered and centrifuged at 100 g in a round-bottomed tube for 5 min to collect protoplasts. Re-suspended protoplasts were purified by floating on a CPW 21S solution (21% [w/v] sucrose-containing CPW solution, pH 5.8), followed by centrifugation at 80 g for 7 min. The purified protoplasts were washed with W5 solution and pelleted by centrifugation at 70 g for 5 min. Finally, protoplasts were re-suspended in W5 solution and counted under the microscope using a hemocytometer.

To isolate *Brassica oleracea* protoplasts, plant protoplasts were isolated from *B. oleracea* cotyledons. A specific method for protoplast isolation is as follows. *B. oleracea* Dongbok seeds were sterilized with a solution containing 70% ethanol and 1% Clorox for 15 minutes, washed three times with distilled water and sown on MS (Murashige and Skoog) solid medium (3% sucrose, 0.8% agar, pH 5.8). Incubation was performed at 25° C. for 5 days. For protoplast isolation, the cotyledons of 5-day *B. oleracea* were isolated and digested with an enzyme solution (cellulase, pectinase, 3 mM MES (2-(N-morpholino)ethanesulfonic acid), and 9% mannitol-containing CPW (cell and protoplast washing solution)) by shaking incubation (35 rpm) for 16 hours at 25° C. in darkness. Then, the enzyme-treated cotyledons were filtered through a 50-µm mesh and centrifuged at 100 g in a ml round-bottomed tube for 5 min. Thereafter, the precipitated protoplasts were washed twice with 9% mannitol CPW. The washed protoplasts were purified with 21% sucrose-containing CPW and centrifuged at 100 g for 5 min. The purified protoplasts were isolated from in the middle of sucrose layer, washed with 9% mannitol CPW, and then centrifuged at 50 g for 5 min. The protoplasts were stored at 4° C. until use for transfection.

Example 2: Protoplast Genome Editing

Prior to transfection, Cas9 protein-containing storage buffer (20 mM HEPES, pH 7.5, 150 mM KCl, 1 mM DTT, and 10% glycerol) was mixed with sgRNA and incubated at room temperature for 10 minutes.

To introduce double strand breaks (DSBs) in lettuce using an RNP complex, 5×10$^5$ protoplast cells were transfected with Cas9 protein (30 µg) premixed with in vitro transcribed sgRNA (60 µg). Specifically, 5×10$^5$ protoplasts prepared in Example 1 were re-suspended in 200 µL MMG solution, mixed gently with 20 µL of RNP complex and 220 µL of freshly prepared PEG solution (40% [w/v] PEG 4000; Sigma No. 95904, 0.2 M mannitol and 0.1 M CaCl$_2$), and then incubated at 25° C. for 10 min in darkness. After incubation, 950 µL of W5 solution (2 mM MES [pH 5.7], 154 mM NaCl, 125 mM CaCl$_2$ and 5 mM KCl) was added slowly. The resulting solution was mixed well by inverting the tube. Then, protoplasts were pelleted by centrifugation at 100 g for 3 min and re-suspended gently in 1 ml of WI solution (0.5 M mannitol, 20 mM KCl and 4 mM MES, pH 5.7). Finally, the protoplasts were transferred into multi-well plates and incubated under dark conditions at 25° C. for 24-48 hours, and genome editing analysis was performed. At the same time, the protoplasts were transferred to lettuce culture medium and subjected to plant regeneration procedures.

In the case of *Brassica oleracea*, 2×10$^5$ protoplast cells were transfected with Cas9 protein (40 µg) premixed with in vitro transcribed sgRNA (15 µg). Specifically, 2×10$^5$ protoplast cells prepared in Example 1 were re-suspended in 200 µL MMG solution (4 mM MES, 0.4 M mannitol and 15 mM MgCl$_2$, pH 5.7), mixed gently with a RNP complex and 220 µL of freshly prepared PEG solution (40% [w/v] PEG 4000; Sigma No. 95904, 0.2 M mannitol and 0.1 M CaCl$_2$), and then incubated at 25° C. for 10 min. Thereafter, the same volume of W5 solution (2 mM MES [pH 5.7], 154 mM NaCl, 125 mM CaCl$_2$ and 5 mM KCl) was added three times at 10-min intervals, centrifuged at 50 g for 5 min, and then re-suspended in W5 solution. The transfected protoplasts were incubated at 25° C. for 24 hours, and then genome editing analysis was performed. At the same time, the protoplasts were transferred to culture medium (MS, 6% myo-inositol, 0.4 mg/L thiamine-HCl, 2 mg/L 2,4-D (dichlorophenoxyacetic acid), 0.5 mg/L BA and 30 g/L sucrose, pH 5.8), incubated at 25° C. for 24 hours, and then subjected to plant regeneration procedures.

Example 3: Protoplast Regeneration

For lettuce protoplast regeneration, RNP-transfected protoplasts were re-suspended in ½×B5 culture medium supplemented with 375 mg/L CaCl$_2$.2H$_2$O, 18.35 mg/L NaFe-EDTA, 270 mg/L sodium succinate, 103 g/L sucrose, 0.2 mg/L 2,4-D, 0.3 mg/L 6-benzylaminopurine (6-BAP), and 0.1 g/L MES. Then, the protoplasts were mixed with a 1:1 solution of ½×B5 medium and 2.4% agarose to a culture density of 2.5×10$^5$ protoplasts/ml. The protoplasts embedded in agarose were plated onto 6-well plates, overlaid with 2 ml of ½×B5 culture medium, and cultured at 25° C. in darkness. After 7 days, the medium was replaced with a fresh culture medium, and the protoplasts were cultured under light conditions (16-hr light [30 µmol m$^{-2}$ s$^{-1}$] and 8-hr darkness) at 25° C. After 3 weeks of culture, micro-calli were grown to a few mm in diameter and transferred to and cultured in MS regeneration medium supplemented with 30 g/L sucrose, 0.6% plant agar, 0.1 mg/L α-naphthalaneacetic acid (NAA), 0.5 mg/L BAP. Induction of multiple lettuce shoots was observed on the regeneration medium after about 4 weeks.

For regeneration of *Brassica oleracea* protoplasts, RNP-transfected protoplasts cultured in culture medium were centrifuged at 50 g for 5 minutes, and the precipitated cells were re-suspended in callus induction medium (MS salt, 6% myo-inositol, 0.4 mg/L thiamine-HCl, 2 mg/L 2,4-D, 0.5 mg/L BA and 30% sucrose, pH 5.8) and cultured at 25° C. for 3 to 4 weeks in darkness. The cultured micro-calli were transferred to callus induction solid medium (MS salt, 0.6% myo-inositol, 0.4 mg/L thiamine-HCl, 2 mg/L 2,4-D, 0.5 mg/L BA, 3 mg/L AgNO$_3$, % sucrose and 0.4% gelrite), pH 5.8) and cultured in a light condition (a 16-hr light cycle with a white fluorescent lamp of about 30 μmol/m$^2$s) at 25° C. Some of the calli were used for evaluation of indel frequency. After 4 weeks of incubation under a light condition, green plantlets regenerated from the calli derived from the genome-edited protoplasts were transferred to MS basal medium to induce root production for regeneration into whole plants.

Example 4: Targeted Deep Sequencing

The on-target sites were amplified from the genomic DNA of RGEN-RNP-transfected protoplasts or regenerated calli. Indices and sequencing adaptors were added by additional PCR. High-throughput sequencing was performed using Illumina Miseq (v2, 300 cycle). The primers used are shown in Table 1 below.

TABLE 1

| | |
|---|---|
| LsBin2-deepF | TAGAAACGGGGGAAACTGTG (SEQ ID NO: 1) |
| LsBin2-deepR | CCCAAAAGAAGCTCAGCAAG (SEQ ID NO: 2) |
| BoGSL-ALK F1_1-5 | GCGAAAAGAATGGGTGCAGA (SEQ ID NO: 3) |
| BoGSL-ALK R1_1-5 | TGGCATCCAAAACTGACTTCT (SEQ ID NO: 4) |
| BoGSL-ALK F2_6-9 | TCGAGTTACCAGTTGAGGCT (SEQ ID NO: 5) |
| BoGSL-ALK R2_6-9 | CGACATGACGTTACCTCATAGTC (SEQ ID NO: 6) |
| BoGSL-ALK F3_10-12 | CAGCGAAACGATCCAGAAGT (SEQ ID NO: 7) |
| BoGSL-ALK R3_10-12 | CTGACCGCAACATTAGCATCA (SEQ ID NO: 8) |
| BoGSL-ALK F4_13-15 | GCGCAGATGATGAGGAGAAG (SEQ ID NO: 9) |
| BoGSL-ALK R4_13-15 | AGAATCTCCAGCCATAACAACG (SEQ ID NO: 10) |

Example 5: T7E1 Assay

Genomic DNA was isolated from protoplasts or calli using DNeasy Plant Mini Kit (Qiagen). The target DNA region was amplified and subjected to the T7E1 assay. In brief, PCR products were denatured at 95° C. and cooled slowly to room temperature using a thermal cycler. Annealed PCR products were incubated with T7 endonuclease I (e.g, ToolGen, Inc.) at 37° C. for 20 min and analyzed via agarose gel electrophoresis.

Example 6: RGEN-RFLP Assay

PCR products (300-400 ng) were incubated in 1×NEB buffer 3 for 60 min at 37° C. with Cas9 protein (1 μg) and sgRNA (750 ng) in a reaction volume of 10 μl. RNase A (4 μg) was then added to the reaction mixture and incubated at 37° C. for 30 min to remove the sgRNA. The reaction was stopped by adding 6× stop solution (30% glycerol, 1.2% SDS, and 250 mM EDTA). DNA products were electrophoresed using 2.5% agarose gel.

Experimental Example 1: Regeneration of Plants from Brassinosteroid Insensitive 2(BIN2) Gene-Disrupted Lettuce Protoplasts The present inventors designed an RNA-guided engineered nuclease (RGEN) target site to disrupt the BRASSINOSTEROID INSENSITIVE 2 (BIN2) gene, which encodes a negative regulator in a brassinosteroid (BR) signaling pathway in lettuce (FIG. 1a; SEQ ID NO: 11). Next, the present inventors transfected the RGEN ribonucleoprotein (RNP) into lettuce protoplasts with polyethylene glycol (PEG) and measured the targeted gene modification efficiencies caused by RGEN using both the T7 endonuclease 1 (T7E1) assay and targeted deep sequencing. As a result, insertions and deletions (indels) were detected at the expected position, that is, 3 nucleotide (nt) upstream of NGG protospacer-adjacent motif (PAM), with frequencies that ranged from 8.3% to 11% using T7E1 assay and 3.2% to 5.7% using NGS assay (FIGS. 1b and 1c).

Next, the present inventors performed a regeneration process to produce plants which comprise the BIN2 variant alleles from RGEN-RNP-treated protoplasts. As a result, only a fraction (<0.5%) of the protoplasts could be cultured to form whole plants via calli (FIGS. 2 and 3). Among these, 35 protoplast lines were used to perform further analyses (FIG. 4). In brief, the present inventors performed the RGEN-RFLP assay and targeted deep sequencing to genotype the lettuce microcalli. RGEN-RFLP assay can distinguish mono-allelic mutant clones (50% cleavage) from heterozygous bi-allelic mutant clones (no cleavage) and homozygous bi-allelic mutant clones (no cleavage) from wild-type clones (100% cleavage). These analyses showed that two of 35 calli (5.75%) contained mono-allelic mutations and 14 of 35 calli (40%) contained bi-allelic mutations at the target site. The above results indicate that genome-edited lettuces were obtained at a frequency of 46% without any selection, which is an extremely high frequency compared to the mutation frequency by RGEN-RNP in bulk populations. This suggests that RGEN-induced mutations in the BIN2 gene were stably maintained and accumulated during the regeneration process.

Experimental Example 2: Regeneration of Plants from Glucosinolate-Oxoglutarate-Dependent Dioxygenase Homolog (GSL-ALK) Gene-Disrupted *Brassica oleracea* Protoplasts In order to confirm the phenomenon of Experimental Example 1 while excluding experimental errors, the present inventors performed an independent experiment in *Brassica oleracea*. Since the possibility that the disruption of the BIN2 gene used as the target in Experimental Example 1 would affect the growth and survival of the protoplasts in the regeneration process, the present inventors screened a gene irrelevant to the growth and survival of the protoplasts or calli. To this end, seven sgRNA sequences (Table 2) were designed in order to target and disrupt the *B. oleracea* glucosinolate-oxoglutarate-dependent dioxygenase homolog (GSL-ALK) gene encoding a protein that affects side chain mutations in the glucosinolate pathway.

TABLE 2

| Name | sgRNA sequence | Mutant reads #/ Total reads # | Indel frequency (%) |
|---|---|---|---|
| BoGSL-ALK 1 | ACTTCCAGTCATCTATCTCT (SEQ ID NO: 12) | 0/27157 | 0 |
| BoGSL-ALK 2 | TGGTCCGAGAGATAGATGAC (SEQ ID NO: 13) | 2/30038 | 0 |
| BoGSL-ALK 7 | CTGCTACGCCCTGATTGTGA (SEQ ID NO: 14) | 261/61752 | 0.4 |
| BoGSL-ALK 9 | GTCTTGTTACCCTCACAATC (SEQ ID NO: 15) | 67/33545 | 0.2 |
| BoGSL-ALK 12 | AGAATGGTCATAGAGAGCTT (SEQ ID NO: 16) | 164/62330 | 0.3 |
| BoGSL-ALK 13 | ATATGAGATTGAAGGTTTGG (SEQ ID NO: 17) | 480/82376 | 0.6 |
| BoGSL-ALK 15 | ACAACGAAAGAGTTATGAGA (SEQ ID NO: 18) | 55/85835 | 0.1 |

The GSL-ALK gene is a gene having no relation to cell survival or stress resistance, and it was expected that a result different from that of Experimental Example 1, that is, a relatively lower efficiency, would be obtained.

First, RGEN-RNP was introduced into *Brassica oleracea* cotyledon-derived protoplasts by PEG (polyethylene glycol)-mediated transfection, and the editing frequency of the target gene was measured using NGS assay. As a result, it was shown that the frequency was in the range of 0.0% to 1% (Table 2).

Next, the present inventors performed a regeneration process to produce whole plants which contain the GSL-ALK gene-edited alleles from RGEN-RNP-transfected protoplasts (FIG. 6). As a result, only a fraction (<0.1%) of the *Brassica oleracea* cotyledon-derived protoplasts could be cultured to form calli. Targeted deep sequencing for the regenerated calli was performed to genotype the *Brassica oleracea* calli. As a result, like the case of BIN2 gene-disrupted lettuce, it was shown that genome-edited calli were present in the analyzed calli at an extremely high frequency (24 to 100%) compared to the editing frequency in protoplast populations (Table 3).

TABLE 3

| Name | The total number of analyzed calli | The number of target gene edited calli | The frequency of edited calli (%) |
|---|---|---|---|
| BoGSL-ALK 1 | 3 | 1 | 33.3 |
| BoGSL-ALK 2 | 10 | 4 | 40.0 |
| BoGSL-ALK 7 | 1 | 1 | 100.0 |
| BoGSL-ALK 9 | 7 | 4 | 57.1 |
| BoGSL-ALK 12 | 25 | 6 | 24.0 |
| BoGSL-ALK 13 | 14 | 4 | 28.5 |
| BoGSL-ALK 15 | 15 | 4 | 26.7 |

The above-described results suggest that when RGEN-RNP is applied, genome-edited protoplasts are stably maintained and accumulated regardless of the kind of target gene in the regeneration process of plant protoplasts. Namely, the present inventors confirmed that when protoplasts are treated with RGEN-RNP, cell proliferation and growth are promoted so that plants can be regenerated with a high efficiency.

From the foregoing, it will be understood by those skilled in the art to which the present invention pertains that the present invention can be carried out in other embodiments without changing the technical spirit or essential feature thereof. In this regard, it should be understood that the aforementioned examples are of illustrative purpose in all aspects but not is limited thereto. The scope of the present invention should be construed to include the meaning and scope of the appended claims, and all the alterations and modified forms which are derived from the equivalent concept thereof, rather than the detailed description.

The invention claimed is:

1. A method for increasing the production efficiency of a genome-edited plant from a plant protoplast, comprising the steps of:
   (i) editing GSL-ALK (Glucosinolateoxoglutarate-dependent dioxygenase homolog) gene of the plant protoplast by direct introduction of a Cas protein-guide RNA ribonucleoprotein (RNP) in which a Cas protein and a guide RNA in the form of naked RNA are pre-assembled into an isolated plant protoplast without using a vector; and
   (ii) producing a GSL-ALK-edited plant by regenerating the plant protoplast,
   wherein the guide RNA is selected from the group consisting of SEQ ID Nos. 12 to 18.

2. The method of claim 1, wherein the editing of a genome is performed by knocking-out.

3. The method of claim 1, wherein the guide RNA is in the form of a dual RNA comprising a crRNA and a tracrRNA, or a single-chain guide RNA (sgRNA).

4. The method of claim 3, wherein the single-chain guide RNA comprises a part of crRNA and a part of tracrRNA.

5. The method of claim 1, wherein the Cas protein is a Cas9 protein or a variant of Cas9 protein in which the catalytic aspartate residue is substituted with another amino acid.

6. The method of claim 1, wherein the Cas protein recognizes NGG trinucleotide.

7. The method of claim 1, wherein the Cas protein is linked to a protein transduction domain.

8. The method of claim 5, wherein the amino acid is alanine.

9. The method of claim 1, wherein the Cas9 protein is derived from the genus *Streptococcus*.

10. The method of claim 9, wherein the genus *Streptococcus* is *Streptococcus pyogenes*.

11. The method of claim 1, wherein the plant protoplast is derived from *Lactuca sativa* or *Brassica oleracea*.

12. The method of claim 1, wherein the introduction is performed by the method selected from the group consisting of microinjection, electroporation, DEAE-dextran treatment, lipofection, nanoparticle-mediated transfection, protein transduction domain-mediated transduction, and PEG-mediated transfection.

13. The method of claim 1, wherein regenerating the plant protoplast comprises the steps of: forming a callus by culturing the plant protoplast; and producing a regenerated plant by further culturing the callus.

14. A plant regenerated from the genome-edited plant protoplast produced by the method of claim 1.

15. A method for producing a genome-edited *Brassica oleracea* plant from a plant protoplast of *Brassica oleracea*, comprising the steps of:
   (i) editing GSL-ALK (Glucosinolateoxoglutarate-dependent dioxygenase homolog) gene a genome of a plant the protoplast of *Brassica oleracea* by introducing a Cas9 protein-guide RNA ribonucleoprotein (RNP) in which a Cas9 protein and a guide RNA in the form of naked RNA are pre-assembled into an isolated plant protoplast of *Brassica oleracea*; and
   (ii) producing a GSL-ALK gene genome-edited *Brassica oleracea* plant by regenerating the plant protoplast of *Brassica oleracea* into a whole plant by forming a callus from the plant protoplast of *Brassica oleracea* and further culturing the callus;
   wherein the plant protoplast is derived from *Brassica oleracea*; and wherein the guide RNA is selected from the group consisting of SEQ ID Nos. 12 to 18.

* * * * *